United States Patent
Wu et al.

(10) Patent No.: US 7,785,639 B2
(45) Date of Patent: Aug. 31, 2010

(54) COMPOSITION FOR TREATING CANCER CELLS AND PREPARATION METHOD FOR THE SAME

(75) Inventors: Yang-Chang Wu, Kaohsiung (TW); An-Shen Lin, Kaohsiung (TW); Fang-Rong Chang, Kaohsiung (TW); Chin-Chung Wu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 12/618,922

(22) Filed: Nov. 16, 2009

(65) Prior Publication Data

US 2010/0081832 A1    Apr. 1, 2010

Related U.S. Application Data

(62) Division of application No. 12/465,925, filed on May 14, 2009, now Pat. No. 7,670,630, which is a division of application No. 11/471,295, filed on Jun. 20, 2006, now Pat. No. 7,550,160.

(30) Foreign Application Priority Data

Nov. 8, 2005    (TW) .............................. 94139201 A

(51) Int. Cl.
*A61K 36/00*    (2006.01)
*A61K 47/00*    (2006.01)
*A61K 9/00*    (2006.01)

(52) U.S. Cl. ........................ 424/725; 424/400; 424/439

(58) Field of Classification Search .................... None
See application file for complete search history.

(56) References Cited

U.S. PATENT DOCUMENTS

2006/0148680 A1 *    7/2006    Kieliszewski et al. .......... 514/8
2008/0242834 A1 *    10/2008    Kieliszewski et al. ....... 530/300

* cited by examiner

*Primary Examiner*—Christopher R Tate
*Assistant Examiner*—Randall Winston
(74) *Attorney, Agent, or Firm*—Trojan Law Offices

(57) ABSTRACT

A composition for treating cancer cells and a preparation method therefor are provided. The novel flavonoid compounds are obtained from natural plants, and more particularly the compounds have a cytotoxicity on cancer cells.

3 Claims, 1 Drawing Sheet

COMPOSITION FOR TREATING CANCER CELLS AND PREPARATION METHOD FOR THE SAME

CROSS-REFERENCE TO RELATED APPLICATIONS

This is a divisional of and claims the benefit of priority from U.S. patent application Ser. No. 12/465,925, filed May 14, 2009 now U.S. Pat. No. 7,670,630, which in turn is a divisional and claims the benefit of U.S. patent application Ser. No. 11/471,295, filed Jun. 20, 2006, now U.S. Pat. No. 7,550,160, the full disclosures of which are incorporated herein by reference.

FIELD OF THE INVENTION

The present invention relates to a composition for treating cancer cells and a preparation method therefor, and more particularly to the composition comprising extracts of *Thelypteris torresiana* and the preparation method therefor.

BACKGROUND OF THE INVENTION

Recently many extracts and their derivatives oriented from natural plants, such as a vincristinem and a vinbalstine, a camptothecin, a taxol and its derivatives, a palitaxel and a docetaxel, have been widely used in clinical chemical therapy of a malignant tumor. Therefore, the effect of the extracts from natural plants has been a burgeoning research in the field of new drug development.

Flavonoids are widely distributed in plants fulfilling many functions including producing yellow or red/blue pigmentation in flowers and protection from attack by microbes and insects. The widespread distribution of flavonoids, their variety and their relatively low toxicity compared to other active plant compounds (for instance alkaloids) mean that many animals, including humans, ingest significant quantities in their diet. Flavonoids have been referred to as "nature's biological response modifiers" because of strong experimental evidence of their ability to modify the body's reaction to allergens, viruses, and carcinogens. They show anti-allergic, anti-inflammatory, anti-microbial and anti-cancer activity. In addition, flavonoids act as powerful antioxidants, providing remarkable protection against oxidative and free radical damage.

As a result, consumers and food manufacturers have become increasingly interested in flavonoids for their medicinal properties, especially their potentially beneficial role in the prevention of cancers and cardiovascular disease. The beneficial effects of fruit, vegetables, and tea or even red wine have been attributed to flavonoid compounds rather than to known nutrients and vitamins. These beneficial effects await further clinical trials in humans.

In view of the above, the inventors of the present invention discover that the crude extracts of *Thelypteris torresiana*, only produced in Taiwan, have cytotoxic activities to the NUGC and HONE-1 cell lines supported by the experimental data through screening several dozens of natural crude extracts based on the inventors' experience in studying the effect of the extracts from natural plants for a long time. To study in advance, it is discovered that the unique novel flavonoid compounds therein have strong cytotoxic activities to human cancer cells, including liver cancer cells (Hep G2, and Hep 3B), breast cancer cells (MCF-7, MDA-MB-231), and lung cancer cells (A549).

SUMMARY OF THE INVENTION

The present invention provides a composition for treating cancer cells and a preparation method therefor, wherein not only the novel flavonoid compounds are obtained from natural plants but also the biological activity thereof is capable of treating cancer cells.

In accordance with one aspect of the present invention, a composition for treating a cancer cell is provided. The composition comprises a flavonoid compound represented by a formula (I):

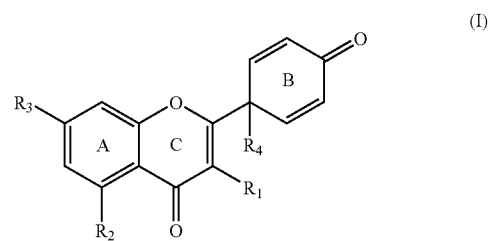

B ring is 4-oxo-cyclohexa-2,5-dienyl group, and the $R_1$, $R_2$, $R_3$ and $R_4$ are respective ones selected from the group consisting of H, OH, $C_{1-12}$-alkyl, $C_{1-12}$-alkoxy, and sugar groups.

According to the present invention, the flavonoid compound is extracted from Pteridophyta.

According to the present invention, the Pteridophyta is *Thelypteris torresiana*.

In accordance with another aspect of the present invention, a composition for treating a cancer cell is provided. The composition comprises a flavonoid compound represented by a formula (II):

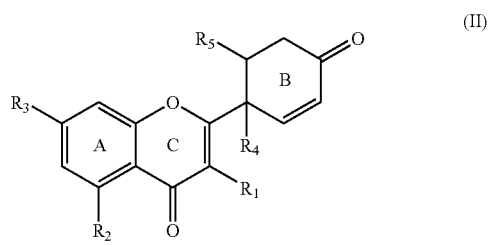

B ring is 4-oxo-cyclohexa-2-enyl group, and the $R_1$, $R_2$, $R_3$, $R_4$, and $R_5$ are respective ones selected from the group consisting of H, OH, $C_{1-12}$-alkyl, $C_{1-12}$-alkoxy, and sugar groups.

According to the present invention, the flavonoid compound is extracted from Pteridophyta.

According to the present invention, the Pteridophyta is *Thelypteris torresiana*.

In accordance with a further aspect of the present invention, a composition for treating a cancer cell is provided. The composition comprises a flavonoid compound represented by a formula (III):

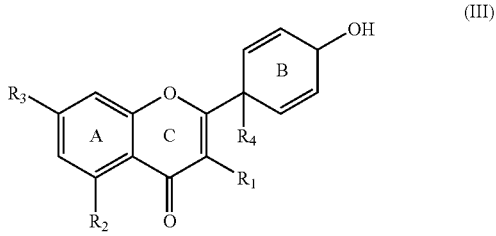

(III)

B ring is cyclohexa-2,5-dienol group, and the $R_1$, $R_2$, $R_3$, and $R_4$ are respective ones selected from the group consisting of H, OH, $C_{1-12}$-alkyl, $C_{1-12}$-alkoxy, and sugar groups.

According to the present invention, the flavonoid compound is extracted from Pteridophyta.

According to the present invention, the Pteridophyta is *Thelypteris torresiana*.

In accordance with further another aspect of the present invention, a method for preparing one of the flavonoid compounds is provided. The following steps are comprised. First, a dried plant is provided. Then, a first extract with a first organic solution from the dried *T. torresiana* is obtained. Next, a second extract with a second organic solution from the first extract is obtained. Finally, the flavonoid compound is obtained by separating the second extract.

According to the above, the first organic solution is a methanol.

According to the above, the second organic solution is an ethyl acetate.

According to the above, the flavonoid compound is separated from the second extract by a chromatography.

The foregoing and other features and advantages of the present invention will be more clearly understood through the following descriptions with reference to the drawings, wherein:

DETAILED DESCRIPTION OF THE PREFERRED EMBODIMENT

Figure 1:
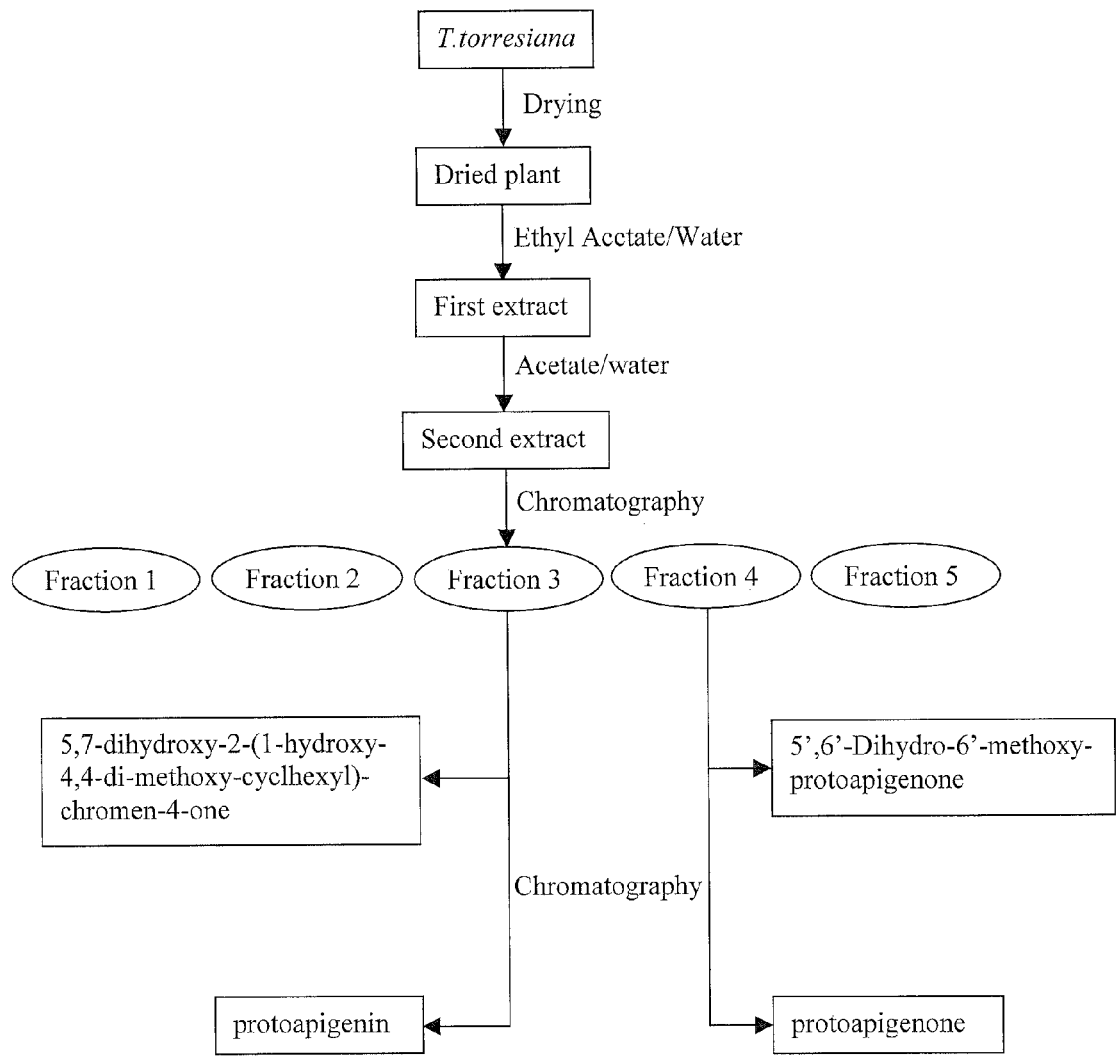
FIG. 1 is a flowchart of the preparation method according to the present invention.

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

The present invention provides a composition for treating cancer cells. The composition comprises a flavonoid compound, which is extracted from *T. torresiana*. The preparation method is illustrated as follows.

Please refer to FIG. 1, which shows a flowchart of the preparation method according to the present invention. In the method of the present invention, 1.5 kilograms of total *T. torresiana*. Plant are gathered and dried, and then two liters of methanol are used to extract the dried *T. torresiana*. Plant for six times repeatedly to obtain a first extract. The first extract is formed as a brown sticky material after decompressing, condensation, and drying, and then the brown sticky material is separated by shaking in the buffer of the acetate and water. A second extract is obtained from the acetate layer through decompressing and condensation. Subsequently, a chromatography is performed to fractionate the second extract using n-Hexane, n-Hexane/acetate (4:1), acetate, methanol, and water respectively in two liters as a mobile phase in the resin of celite 545 to obtain five fractions (T1-T5).

The fraction T4 is further processed repeatedly by chromatography in the silica gel column using a chloroform/methanol as a mobile phrase. By means of the preparation method, a huge amount of the flavonoid compound, named as protoapigenone, can be obtained.

During the above separation process of T4 fraction, a pure compound, whose polarity is less than the protoapigenone, is obtained in a tiny amount using a chloroform/methanol as a mobile phrase. The pure compound is also a flavonoid compound, named as 5',6'-dihydro-6'-methoxyprotoapigenone.

The fraction T3 is separated through a preparative high-performance liquid chromatography using a methanol/water (50:50) as a mobile phrase. In the condition of 3.5 ml/min flow rate, a novel flavonoid compound is obtained, named as protoapigenin, at $t_R$=15.5 min. However, another novel compound is obtained, named as 5,7-dihydro-2-(1-hydroxy-4,4-dimethoxy-cyclohexyl)-chromen-4-one, in the same condition.

According to the preparation method of the present invention, there are four novel flavonoid compounds obtained, and their respective properties are identified and described as follows.

With regard to the protoapigenone, it is a needle crystal with light yellow color and its pseudo molecule ion peak m/z is 287.0553 $[M+H]^+$ with the molecular formula being $C_{15}H_{10}O_6$. In the $^1H$ NMR spectrum thereof, there is the signal that indicates the chemical shift of B ring is respectively $\delta$7.23 and $\delta$6.52 (which indicates two hydrogen, doublet, and the coupling constant being 10.2). The signal is presented in a special AA'XX' system. Further, there is a signal of $\delta$185.2 indicating a keto group at the 4' position according to the $^{13}C$ NMR spectrum. Furthermore, there is a set of retro-Diels-Alder split signals at C-ring in flavonoids, m/z $[M-152]^+$ and $[M-133]^+$, from analyzing the fragments in the mass spectrum.

As for the physical properties of the protoapigenone, this compound has the following properties: m.p. 180-181° C.; UV (MeOH): $\lambda_{max}$ 325, 299, 259, 249, 230, and 206 nm; IR: $\upsilon_{max}$ 3224, 2928, 1656, 1621, 1597, 1349, and 1164 $cm^{-1}$; $^1H$ NMR (200 MHz, pyridine-$d_5$): $\delta$=13.31 (1H, br s, OH-5), 7.23 (2H, d, J=10.2 Hz, H-2', H-6'), 7.05 (1H, s, H-3), 6.72 (1H, d, J=2.2 Hz, H-8), 6.59 (1H, d, J=2.2 Hz, H-6), 6.52 (2H, d, J=10.2 Hz, H-3', H-5'). EI-MS m/z (rel. int.): 286 $[M]^+$ (100), 270 (39), 242 (18), 229 (31), 153 (33), 134 (12); HR-ESI-MS: m/z 287.0553 $[M+H]^+$ (Calculated for $C_{15}H_{11}O_6$, 287.0550).

With regard to 5',6'-dihydro-6'-methoxyprotoapigenone, it is a light yellow solid and its pseudo molecule ion peak m/z is 319.0814 $[M+H]^+$ with the molecular formula being $C_{16}H_{15}O_7$. Its ultraviolet and infrared spectrum is similar to the protoapigenone, indicating that the compound has the typical skeleton of flavonoid compounds. The 5',6'-dihydro-6'-methoxyprotoapigenone is derived from the reduction of the double bond between 5' and 6' positions, and the 6' position of the protoapigenone is replaced with a methoxyl group based on the analysis of 1D and 2D NMR spectrum signals. A retro-Diels-Alder (RDA) signal, m/z $[M-165]^+$, of C-ring in flavonoids is obtained by analyzing the fragments in the mass spectrum. This compound has the following properties: m.p. 162-163° C.; UV (MeOH): $\lambda_{max}$ 326, 297, 254, 232, 212 nm; IR: $\upsilon_{max}$ 3350, 2940, 1658, 1624, 1583, 1352, 1165 $cm^{-1}$; $^1H$ NMR (400 MHz, pyridine-$d_5$) $\delta$=13.42 (1H, br s, OH-5), 7.13

(1H, d, J=10.0 Hz, H-2'), 7.12 (1H, s, H-3), 6.77 (1H, d, J=2.0 Hz, H-8), 6.75 (1H, d, J=2.0 Hz, H-6), 6.38 (1H, d, J=10.0 Hz, H-3'), 4.33 (1H, dd, J=9.2, 4.4 Hz, H-6'), 3.31 (3H, s, OCH$_3$), 3.21 (1H, dd, J=16.0, 9.2 Hz, H-5'a), 3.15 (1H, dd, J=16.0, 4.4 Hz, H-5'b); EI-MS m/z (rel. int.); 318 [M]$^+$ (19), 260 (100), 232 (39), 218 (19), 204 (36), 203 (35), 153 (7); HR-ESI-MS: m/z 319.0814 [M+H]$^+$ (Calculated for C$_{15}$H$_{11}$O$_6$, 319.0812).

With regard to protoapigenin, it is a light yellow solid and its false molecule ion peak m/z is 289.0714 [M+H]$^+$ with the molecular formula being C$_{15}$H$_{12}$O$_6$. Its $^{13}$C NMR spectrum signal is similar to that of the protoapigenone, and the apparent difference is the vanished signal of δ185.2 and the additional signal of δ61.9, which indicates that the ketonyl group at the 4' position of the protoapigenone is reduced to a hydroxyl group. Further, its $^1$H NMR spectrum and 2D NMR signals are also in support of the above result. Therefore, a set of retro-Diels-Alder (RDA) signals, m/z [M−153]$^+$ and [M−136]$^+$, at C-ring in flavonoids are obtained by analyzing the fragments in the mass spectrum. This compound has the following properties: m.p. 192-193° C.; UV (MeOH): λ$_{max}$ 323, 299, 258, 249, 2320 nm; IR: ν$_{max}$ 3356, 2924, 1656, 1610, 1553, 1368, 1073 cm$^{-1}$; $^1$H NMR (400 MHz, pyridine-d$_5$) δ=13.52 (1H, br s, OH-5), 6.90 (1H, s, H-3), 6.71 (1H, d, J=2.4 Hz, H-8), 6.54 (1H, d, J=2.4 Hz, H-6), 6.53 (2H, dd, J=10.2, 1.6 Hz, H-2', H-6'), 6.36 (2H, dd, J=10.2, 3.2 Hz, H-3', H-5'), 4.78 (1H, m, H-4'); EI-MS m/z (rel. int.): 288 [M]$^+$ (35), 270 (28), 194 (20), 153 (82), 124 (43), 121 (76), 111 (60), 69 (100); HR-ESI-MS: m/z 289.0714 [M+H]$^+$ (Calculated for C$_{15}$H$_{11}$O$_6$, 289.0712).

With regard to the 5,7-dihydroxy-2-(1-hydroxy-4,4-dimethoxy-cyclohexyl)-chromen-4-one, it is a light yellow solid and its pseudo molecule ion peak m/z is 359.1106 [M+H]$^+$ with the molecular formula being C$_{17}$H$_{20}$O$_7$Na. The 1D and 2D NMR spectrums indicate that this compound has the similar skeleton of flavonoids, and only the alkenyl groups on 2', 3', 5', and 6' positions at B-ring is reduced to alkyl groups. It is also found that the signals at 3' and 5' positions have a tendency towards a high magnetic field. Therefore, it is concluded that there are two methoxyl groups at 4' position. This compound has the following properties: $^1$H NMR (400 MHz, pyridine-d$_5$) δ=13.57 (1H, br s, OH-5), 6.97 (1H, s, H-3), 6.75 (1H, d, J=2.0 Hz, H-8), 6.69 (1H, d, J=2.0 Hz, H-6), 3.22 and 3.19 (each 3H, s, OCH$_3$, exchangeable), 2.33 (2H, td, J=13.6, 3.6 Hz, H-2a, 6a), 2.21 (2H, td, J=13.6, 3.6 Hz, H-3a, 5a), 2.07 (2H, br.d, J=13.6, H-3b, 5b), 1.99 (2H, br.d, J=12.6, H-2b, 6b); HR-ESI-MS: m/z 359.1106 [M+H]$^+$ (calculated for C$_{15}$H$_{11}$O$_6$Na, 359.1107).

Furthermore, the above four novel flavonoid compounds of the is present invention are tested for their biological activities. There are five human cancer cell lines for a biological activity testing, including two human breast cancer cell lines (MCF-7 and MDA-MB-231), two human liver cancer cell lines (Hep G2 and Hep 3B), and one human lung cancer cell line (A549). Besides, there is one human breast epidermal cell (MCF-10A) as a normal control. Human cancer cells are from American Type Culture Collection, and incubated in the RPMI-1640 suspension with the additives of the 10% (v/v) fetal calf serum, 100 U/ml penicillin, and 100 μg/ml streptomycin under the condition of 37° C., 5% carbon dioxide, and 95% fresh air. Subsequently, the MCF-10A cell line is incubated in 50% Dulbecco's modified Eagle's buffer and the 50% Ham's F-12 buffer with 10 μg/ml cow trypsin, 20 ng/ml EGF, 100 ng/ml cholera enterotoxin, 0.5 μg/ml hydrocortisone, and 10% fetal calf serum.

In the present invention, the cytotoxic testing experiment is analyzed in the method of MTT (3-(4,5-dimethyl-thiazol-2-yl)-2,5-diphenyl tetrazolium bromide) known in the prior art. The respective five cancer cell lines and the normal cell line (MCF-10A) are incubated within the microplate with 96 wells in the density of 5,000-10,000 cells/well. The next day the detected compounds (A-D) and Doxorubicin (compound E) are used to treat the cells. Subsequently, the treated cells are dissolved in DMSO according to the MTT method. Finally, the testing result is obtained by detecting the absorption at 550 nm to analyze the cytotoxic activities of respective compounds. The testing result is shown in Table 1. The value of IC$_{50}$ represents the compound concentration for inhibiting 50% cells growth, and is the Doxorubicin (compound E) having a cytotoxicity on cancer cells is served as a positive control.

| Compound | IC$_{50}$ (μg/mL)$^a$ | | | | | |
|---|---|---|---|---|---|---|
| | Hep G2 | Hep 3B | MCF-7 | A549 | MDA-MB-231 | MCF-10A |
| A | 1.60 ± 0.33 | 0.23 ± 0.01 | 0.78 ± 0.02 | 3.88 ± 0.02 | 0.27 ± 0.02 | 7.9 ± 1.3 |
| B | 5.88 ± 0.47 | 1.74 ± 0.08 | 5.92 ± 0.29 | 13.30 ± 0.23 | 1.30 ± 0.10 | *$^c$ |
| C | 1.60 ± 0.33 | 20.00 ± 0.58 | — | 18.84 ± 0.60 | — | * |
| D | —$^b$ | — | — | — | — | * |
| E | 0.15 ± 0.00 | 0.26 ± 0.06 | 0.32 ± 0.08 | 0.36 ± 0.04 | 0.31 ± 0.02 | * |

Compound A: Protoapigenone
Compound B: 5',6'-Dihydro-6'-methoxy-protoapigenone
Compound C: Protoapigenin
Compound D: 5,7-dihydroxy-2-(1-hydroxy-4,4-dimethoxy-cyclohexyl)-chromen-4-one
Compound E: Doxorubicin
$^a$The data is represented as the average value ± standard deviation (n = 2)
$^b$Without the cytotoxical activity in the concentration of 20 μg/ml
$^c$The test is not performed As shown in Table 1, the protoapigenone, 5',6'-dihydro-6'-methoxy-protoapigenone, and protoapigenin are proved to have good cytotoxic activities on cancer cells.

According to the past literatures, Peterson J. et al (*Nutrition Research* 1998) disclosed that the general flavonoid compounds only have a weak cytotoxity. However, 1-oxygenated 4-oxo-cyclohexa-2,5-dienyl group, 4-oxo-cyclohexa-2-enyl group, cyclohexa-2,5-dienol or cyclohexanel group at B-ring in the flavonoid compounds of the present invention are extracted and identified. The biological activities thereof confirm that the novel compounds disclosed in the present invention have good cytotoxicity on five human cancer cell lines. Therefore, these kind of special flavonoid compounds indicate their unique biological activity, and more particularly, the protoapigenone of the present invention has weak cytotoxicity to normal human breast epidermal cells, which implies one compound with the 1-oxygenated 4-oxo-cyclohexa-2,5-dienyl group at B-ring is a selectivity marker for cancer cells. Therefore, the above unique biological activity is apparently different from the general flavonoid compounds.

According to the above, a composition for treating cancer cells and its preparation method of the present invention not only obtains the novel flavonoid compounds from natural *T. torresiana* but more particularly the biological activity thereof with a cytotoxicity.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A composition for treating cancer cells, comprising an effective amount of an isolated flavonoid compound of a formula (III):

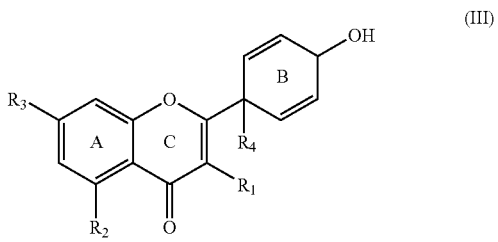

wherein B ring is cyclohexa-2,5-dienol group, and the $R_1$, $R_2$, $R_3$, and $R_4$ are irrespective ones selected from the group consisting of H, OH, $C_{1-12}$-alkyl, $C_{1-12}$-alkoxy, and sugar groups.

2. The composition of claim 1, wherein the isolated flavonoid compound is extracted from *Pteridophyta*.

3. The composition of claim 2, wherein the *Pteridophyta* is *Thelypteris torresiana*.

* * * * *